(12) United States Patent
Bulloch et al.

(10) Patent No.: US 7,959,439 B2
(45) Date of Patent: Jun. 14, 2011

(54) APPARATUS, SYSTEM, AND METHOD FOR IMPLANTING DENTAL PROSTHESIS

(75) Inventors: Scott E. Bulloch, W. St. George, UT (US); Russell G. Olsen, Cedar City, UT (US)

(73) Assignee: Intrinsic Medical, LLC, Cedar City, UT (US)

(*) Notice: Subject to any disclaimer, the term of this patent is extended or adjusted under 35 U.S.C. 154(b) by 250 days.

(21) Appl. No.: 12/257,071

(22) Filed: Oct. 23, 2008

(65) Prior Publication Data

US 2010/0105005 A1    Apr. 29, 2010

(51) Int. Cl.
*A61C 8/00* (2006.01)

(52) U.S. Cl. ......................................... 433/173; 433/172

(58) Field of Classification Search ............... 433/168.1, 433/169, 170, 172, 173, 174, 175, 176
See application file for complete search history.

(56) References Cited

U.S. PATENT DOCUMENTS

| | | | |
|---|---|---|---|
| 3,787,975 A * | 1/1974 | Zuest .............................. 433/182 |
| 4,431,416 A * | 2/1984 | Niznick .......................... 433/174 |
| 4,488,875 A | 12/1984 | Niznick |
| 4,645,453 A | 2/1987 | Niznick |
| 4,932,868 A | 6/1990 | Linkow et al. |
| 4,993,950 A | 2/1991 | Mensor, Jr. |
| 5,071,350 A * | 12/1991 | Niznick .......................... 433/173 |
| 5,073,110 A | 12/1991 | Barbone |
| 5,178,539 A | 1/1993 | Peltier et al. |
| 5,195,891 A | 3/1993 | Sule |
| 5,302,125 A | 4/1994 | Kownacki et al. |
| 5,413,480 A | 5/1995 | Musikant et al. |
| 5,417,570 A | 5/1995 | Zuest et al. |
| 5,480,304 A * | 1/1996 | Nardi ............................. 433/172 |
| 5,556,280 A | 9/1996 | Pelak |
| 5,584,629 A | 12/1996 | Bailey et al. |
| 5,607,304 A | 3/1997 | Bailey |
| 5,989,028 A | 11/1999 | Niznick |
| 5,993,212 A | 11/1999 | Shiner |
| 6,217,332 B1 | 4/2001 | Kumar |
| 6,227,856 B1 | 5/2001 | Beaty et al. |
| 6,273,720 B1 * | 8/2001 | Spalten ......................... 433/173 |
| 6,302,693 B1 * | 10/2001 | Mena ............................. 433/172 |
| 6,358,052 B1 | 3/2002 | Lustig et al. |
| 6,500,003 B2 | 12/2002 | Nichinonni |
| 6,843,653 B2 | 1/2005 | Carlton |
| 7,033,174 B2 | 4/2006 | Giorno |
| 7,214,063 B2 | 5/2007 | Cohen |

OTHER PUBLICATIONS

PCT/US2009/061925, International Search Report and Written Opinion, Jun. 11, 2010.

* cited by examiner

*Primary Examiner* — John J Wilson
(74) *Attorney, Agent, or Firm* — Kunzler Needham Massey & Thorpe (57) ABSTRACT

Described herein are various embodiments of a dental prosthesis implant system and associated apparatus and methods that overcome at least some shortcomings of the prior art. According to one representative embodiment, a connector for an implant retained prosthesis includes a first portion securable to a prosthesis and a second portion securable to an implant embeddable within a bone under a gingival layer. The first portion includes a first engagement element. The second portion includes a second engagement element that defines an internal cavity. The first engagement element is positionable within the internal cavity. When the second portion is secured to the implant and the first engagement element is positioned within the internal cavity, at least a portion of the internal cavity and first engagement element is within the gingival layer. In one implementation, the first portion is coupleable to the second portion via a snap-fit connection.

24 Claims, 5 Drawing Sheets

APPARATUS, SYSTEM, AND METHOD FOR IMPLANTING DENTAL PROSTHESIS

FIELD

This invention relates to dental implants and more particularly relates to removable dental prosthesis implantation.

BACKGROUND

Two-piece attachment systems have been utilized to removably couple a dental prosthesis to an implant embedded within the jaw bone. Typically, such systems include opposing connectors that engage each other to secure the prosthesis to the jaw. In some systems, each connector is secured to one of the dental prosthesis and the implant. To attach the dental prosthesis to the jaw, the dental prosthesis is positioned relative to the jaw such that the connectors engage each other. Ideally, the prosthesis is mounted substantially flush with the gingival (gum) layer covering the bone. In certain systems, the dental prosthesis is removable from the jaw, by pulling the dental prosthesis away from the jaw to disengage the connectors.

Conventional two-piece dental implant attachment systems suffer from several shortcomings. For example, the connector secured to the implant usually rises a significant distance above the gingival level covering the bone. Accordingly, the connector secured to the dental prosthesis must be longer to accommodate the connecter secured to the implant. For applications in which the prosthesis is desirably mounted flush with the gingival level, the thickness of the prosthesis must be thick enough to accommodate the extra length of the connector secured to the prosthesis. Therefore, the configuration of some conventional two-piece dental implant attachment systems places some constraints on the minimum thickness of the prosthesis. In other words, the excessive amount of vertical space between the gingival layer and the prosthesis found in many conventional dental implant systems often place burdening limitations on the design and size of dental prosthesis. Moreover, longer connectors extending above the gingival layer may result in less comfortable, stable, and aesthetically pleasing prosthesis.

Further, some conventional dental implant systems do not provide a movable, e.g., pivotal, connection between the connector secured to the implant and the connector secured to the prosthesis. Similarly, some dental implant systems do not provide a removable connection between these connectors.

SUMMARY

The subject matter of the present application has been developed in response to the present state of the art, and in particular, in response to the problems and needs in the art that have not yet been fully solved by currently available dental prosthesis implant systems. Accordingly, the subject matter of the present application has been developed to provide a dental prosthesis implant system and associated apparatus and methods that overcome at least some shortcomings of the prior art.

According to one representative embodiment, a connector for an implant retained prosthesis includes a first portion securable to a prosthesis and a second portion securable to an implant embeddable within a bone under a gingival layer. The first portion includes a first engagement element. The second portion includes a second engagement element that defines an internal cavity. The first engagement element is positionable within the internal cavity. When the second portion is secured to the implant and the first engagement element is positioned within the internal cavity, at least a portion of the internal cavity and first engagement element is within the gingival layer. In one implementation, the first portion is coupleable to the second portion via a snap-fit connection.

According to one implementation, the connector includes a retention device coupled to the second engagement element. The retention device is configured to removably retain the first engagement element within the internal cavity. The retention device can be formed of a one-piece construction with the second portion. The retention device also can be positioned at least partially within the internal cavity and include an insert nestably engaged with the second engagement element. In certain instances, the retention device includes at least one resiliently movable element. In one specific implementation, the retention device includes an o-ring. According to some implementations, the retention device comprises one of a plurality of retention strengths.

In one representative implementation, the second portion forms a monolithic one-piece construction with the implant.

The first engagement element of the connector can include a ball and the second engagement element can include a socket. When the second portion of the connector is secured to the implant and the first engagement element is positioned within the internal cavity, the second portion can extend a distance less than about six millimeters out of the gingival layer. In some instances, the height of the second portion is less than the height of the first portion.

According to another embodiment, a system for an implant retained prosthesis includes a connection and an implant. The connection includes a prosthesis connection, an abutment, and a retention device. The prosthesis connection includes a ball and a bonding surface configured to bond to a dental prosthesis. The abutment includes a socket defining an internal cavity configured to receive the ball. The retention device is configured to removably retain the ball within the abutment. Regarding the implant, it is connectable to the abutment and embeddable within a bone, which is covered by a gum layer having an outer surface. When the implant is embedded within the bone and the implant is connected to the abutment, at least a portion of the internal cavity is positioned between the bone and the outer surface of the gum layer.

In some implementations, the retention device includes a compliant material disposed within the abutment. The retention device can be made of a polymeric material. The retention device can be removably retained within the abutment. Further, in certain instances, the retention device includes a snap insert configured to generate an audible signal in response to the ball being removably retained within the retention device.

When the implant is embedded within the bone, the implant is connected to the abutment, and the ball is removably retained within the retention device, at least a portion of the ball is positioned between the bone and the outer surface of the gum layer. In some instances, at least one-half of the internal cavity and at least one-half of the ball are positioned between the bone and the outer surface of the gum layer.

The abutment extends outward beyond the outer surface of the gum layer a first distance and the prosthesis connection extends into the prosthesis a second distance. In certain instances, the ratio of the second distance to the first distance is less than about 0.50.

According to yet another embodiment, a method for securing prosthesis to a patient includes fixedly securing an implant to a bone of the patient where the bone is covered by a gingival layer defining an outer surface. The method also includes coupling a socket element having a female engagement portion to the implant where at least a portion of the female engagement portion is between the bone and the outer surface of the gingival layer. Additionally, the method includes inserting a male engagement portion of a connector element into the female engagement portion such that at least a portion of the male engagement portion is between the bone and the outer surface of the gingival layer. The connector element is secured to a prosthesis.

In some implementations, the method includes coupling a retention device to the female engagement portion. In such implementations, inserting the male engagement portion into the female engagement portion comprises engaging the male engagement portion with the retention device such that the male engagement portion is removably retained within the female engagement portion.

According to various implementations, the socket element is a first socket element and the retention device is a first retention device. In such implementations, the method can further include removing the first socket element from the implant and coupling a second socket element to the implant. The second socket element can have a second retention device coupled thereto. The second retention device can be different than the first retention device.

In some instances of the method, coupling a socket element to the implant includes forming the socket element integral with the implant.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

Furthermore, the described features, advantages, and characteristics of the subject matter of the present disclosure may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments. These features and advantages will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

Furthermore, the details, including the features, structures, or characteristics, of the subject matter described herein may be combined in any suitable manner in one or more embodiments. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the disclosed subject matter.

Generally, described herein are embodiments of a dental prosthesis implant system, apparatus, and associated methods that reduce the amount of vertical space above a gingival line occupied by dental prosthesis connectors. In certain embodiments, the dental prosthesis implant system includes a female attachment portion secured to an implant and a male attachment portion secured to a dental prosthesis. The dental prosthesis is secured to the patient via a removable engagement between the male and female attachment portions. When the dental prosthesis is properly secured to the patient, at least a portion of the male and female attachment portions are below the patient's gingival line.

Figure 1:
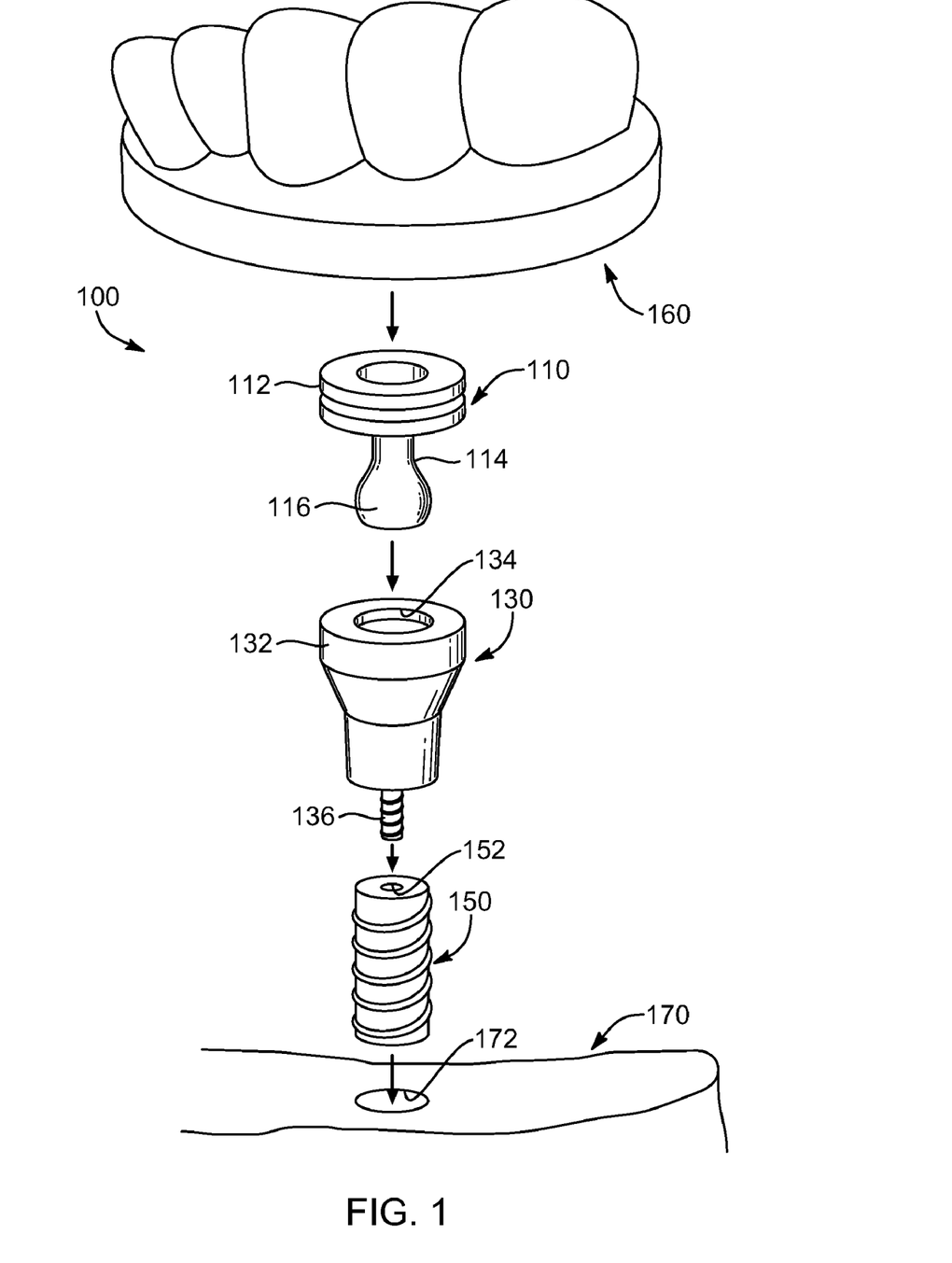
FIG. 1 is an exploded perspective view of a dental prosthesis implant system according to one representative embodiment.

Referring to FIG. 1, a dental prosthesis implant system 100 removably coupling a dental prosthesis 160 to a patient's mouth or jaw 170 is shown. The system 100 includes a male connector 110, a female connector 130, and an implant 150. The male connector 110 is secured to the prosthesis 160 and the implant 150 is secured to the patient's jaw 170. Generally, the female connector 130 is coupled to the implant 150 and the male connector 110 is removably inserted into the female connector 130 to removably secure the prosthesis 160 to the jaw 170.

The dental prosthesis 160 can be any of various dental prosthesis known in the art. For example, as shown, the dental prosthesis 160 is a denture for replacing one or more missing teeth. The denture 160 is made of a hardened polymer and includes one or more artificial teeth formed in the polymer. The denture 160 is constructed using a mold of the patient's mouth. From the mold, the shape of the polymer and location of the teeth relative each other and the polymer can be determined. Typically, the denture 160 is formed to seat onto the patient's gingival (e.g., gum) layer.

Figure 2:
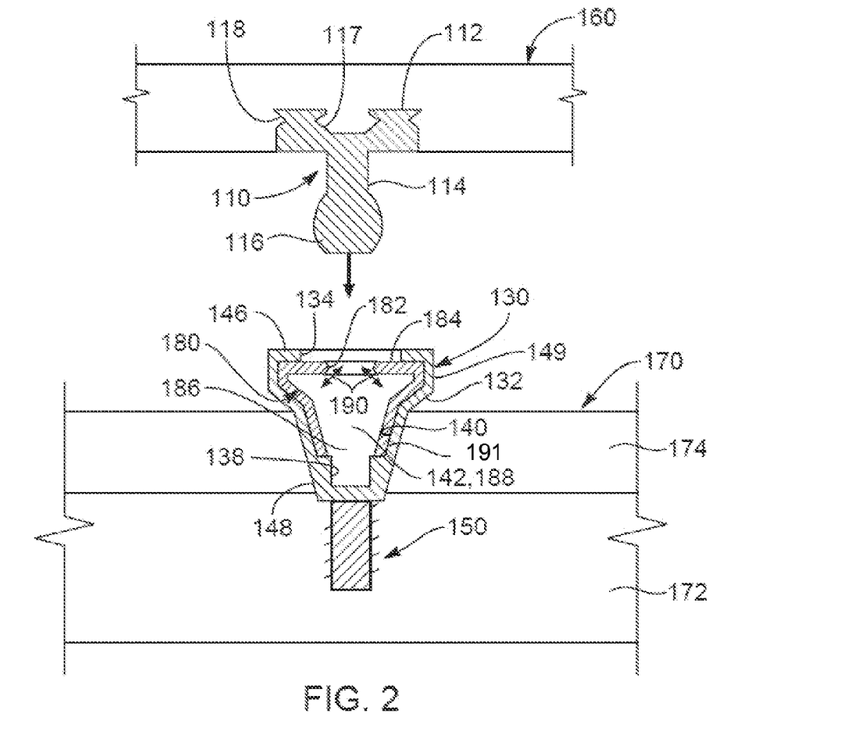
FIG. 2 is an exploded cross-sectional side view of the system of claim 1.

The male connector 110 includes a base 112 and a male engagement portion 114. Referring to FIG. 2, the base 112 is formed in, or otherwise secured to, the polymer. In other words, in the illustrated embodiments, the polymer of the denture 160 is formed around the base 112. The base 112 includes various features for enhancing the connection between the base and the denture 160. For example, the base 112 includes a partially enclosed recess 117 and an annular ridge 118 extending about a circumference of the base. As the denture 160 is formed, the polymer fills the spaces defined by the recess 116 and ridge 118 to resist dislodging of the male connector 110 from the denture 160. The patient's mold is utilized to determine the desired locations of the male connector 110 on the denture 160. As will be explained in more detail below, the male connector 110 is positioned to correspond with the location of a respective female connector 130 secured to the patient's jaw.

As shown, the male engagement portion 114 extends away from the base 112 and includes a generally ball-shaped engagement element 116. Although in the illustrated embodiment the engagement element is ball-shaped, in other instances, the engagement element can have any of various shapes, sizes and configurations suitable for insertion into a female connector, such as female connector 130.

The female connector 130 includes a socket portion 132 extending between an inlet opening 134 and a fastener 136. The inlet opening 134 is sized to receive the engagement element 116 of the male engagement portion 114. The fastener 136 may be a threaded screw configured to threadably engage a threaded aperture 152 formed in the implant 150. Accordingly, in at least one embodiment, the female connector 130 is coupled to the implant 150 by threadably engaging the fastener 136 with the aperture 152 and tightening the female connector 130 against the implant. To facilitate tightening of the female connector 130 to the implant 150, the socket portion 132 defines an internal recess 138 shaped to receive a tightening tool, such as an Allen® wrench. Although not shown, in another embodiment, the female connector 130 is formed integrally, e.g., as a one-piece monolithic construction, with the implant 150. In such embodiments, the internal recess 138 can be used to tighten the implant and female connector combination to the jaw 170.

Figure 5:
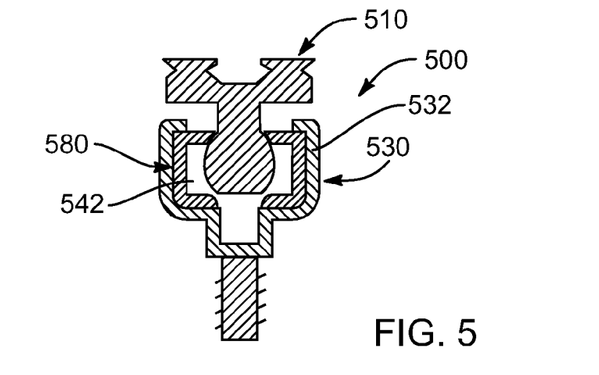
FIG. 5 is a cross-sectional side view of a dental prosthesis implant system according to another embodiment.

Referring to FIG. 2, an internal surface 140 of the socket portion 132 defines an internal cavity 142 extending from the inlet opening 134 of the socket portion 132 to the internal recess 138. The socket portion 132 can have any of various shapes and sizes. The internal cavity 142 can have any of various shapes and sizes that can correspond to the shape and size of the socket portion. In the illustrated embodiment, the socket portion 132 includes a generally conical-frustum shaped portion 148 coupled to a cylindrical shaped portion 149. However, the socket portion 532 of the female connector 530 of FIG. 5 is generally cylindrical-shaped to define a generally cylindrical-shaped internal cavity 536. In other embodiments, particular those in which the inlet opening 134 sits approximately flush with the outer surface 176 of the gingival layer (as will be described in more detail below), the entire socket portion 132 can have a generally conical-frustum shape. In general, the internal cavity 142 has more vertical space for receiving the male connector 110 than the internal cavity 542.

Figure 8:
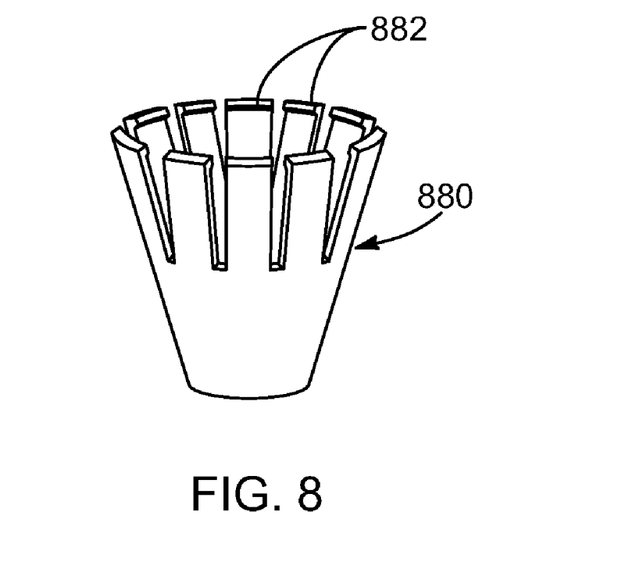
FIG. 8 is a elevation side view of a retention device insert according to one representative embodiment.

Referring again to FIG. 2, the system 100 includes a retention device 180. The retention device 180 defines an aperture 182 proximate the inlet opening 134 of the socket portion. The aperture 182 is sized such that a major dimension of the aperture 182 is smaller than a major dimension of the male engagement portion 114. The retention device 180 includes at least one resiliently movable member 184. Desirably, the at least one resiliently movable member 184 is coextensive with the aperture 182 such that the movable member defines a portion of the aperture 182. As shown in FIG. 8, the retention device 880 includes a plurality of resiliently movable members, e.g., tabs 882. The resiliently movable member 184 is biased in a first non-flexed position (see, e.g., FIG. 2) and configured to flex inward, as shown by directional arrows 190, in response to an inwardly directed force (see, e.g., directional arrow 118) sufficient to overcome the bias of the resiliently movable members. Similarly, the resiliently movable member 184 is configured to flex outward, as shown by directional arrows 190, in response to an outwardly directed force (e.g., an direction opposite the direction arrow 118) sufficient to overcome the bias of the resiliently movable members 184, 882.

Figure 7:
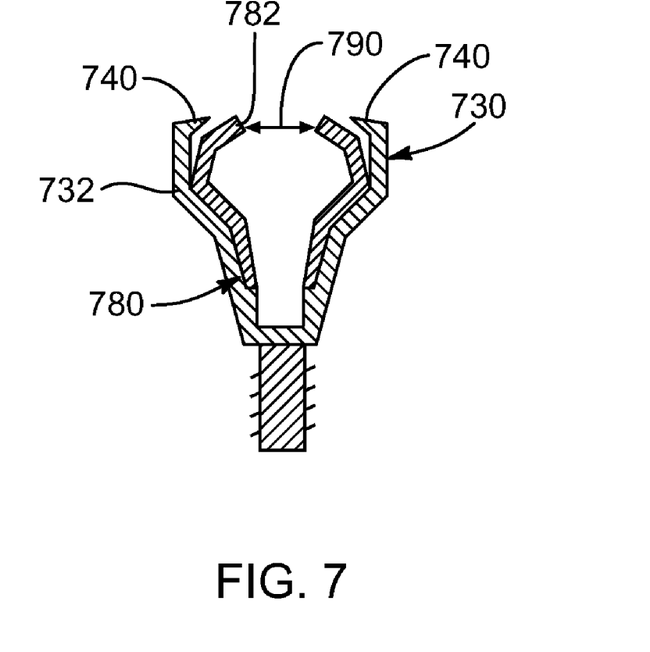
FIG. 7 is a cross-section side view of a socket element of a dental prosthesis implant system according to one embodiment.

In an alternative embodiment of a female connector 730 shown in FIG. 7, the resiliently movable members 782 of retention device 780 are configured to flex laterally away from each other, as shown by directional arrows 790, in response to an inwardly or outwardly directed force.

Figure 4:
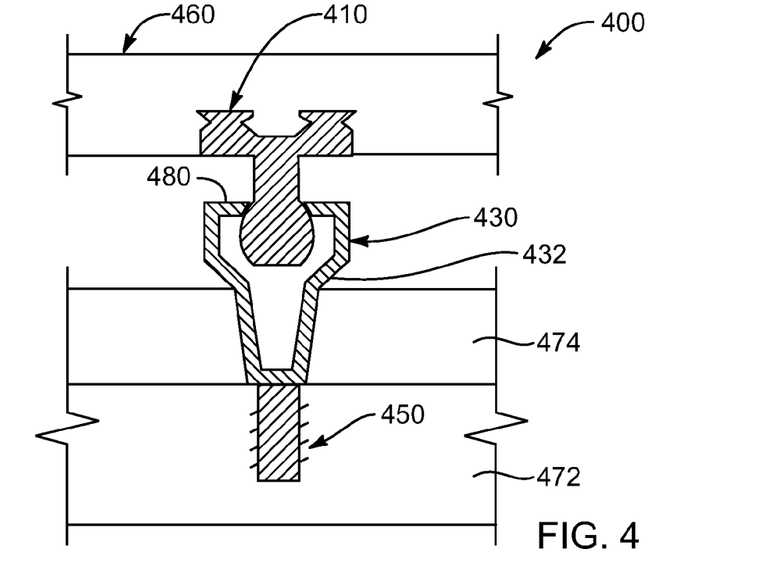
FIG. 4 is a cross-sectional side view of a dental prosthesis implant system having an integrated retention device according to one representative embodiment.

The retention devices of the present embodiments can be separate from the female connectors (see, e.g., retention devices 180, 780, 880) or formed integral with the female connectors (see, e.g., retention device 480 of female connector 430 shown in FIG. 4).

In embodiments where the retention device is separate from the female connectors, the retention device can be an insert positionable within the internal cavity of the female connector. With reference to retention device 180, the device or insert includes an internal cavity 188 that extends from the aperture 182, which can be defined as an outer aperture, to an inner aperture 186. As shown in FIG. 2, the retention device 180 includes an outer surface 191 contoured to matingly engage the internal surface 140 of the socket portion 132 such that the retention device is nestably engaged with the socket portion. The retention device 180 includes a relatively thin-walled construction and the internal cavity 188 of the retention device is coextensive with the internal cavity 142 of the socket portion 132. Further, the retention device 180 is retained within the socket portion 132 due to the major dimension of the inlet opening 134 being less than the major dimension of the retention device 180. More specifically, the socket portion 132 includes an overhang 146 that restricts outward movement of the retention device 180.

Similar to retention insert 180, at least a portion of the retention insert 780 is matingly engaged with the female connector 730. However, the retention insert 780 is configured to be spaced apart from the female connector 730 at a location proximate the resiliently movable members 782 such that the movable members 782 can move laterally toward and away from the female connector. Similar to the female connector 130, the female connector 730 includes an overhang 740 that restricts outward movement of the retention device 780.

In certain embodiments, the retention inserts 180, 580, 780, 880 are made of a material different than the material of the respective female connectors 130, 530, 730. For example, the retention inserts 180, 580, 780, 880 can be made of a polymer, such as a hardened plastic, and the female connectors 130, 530, 730 can be made of a metal or metal alloy, such as aluminum, steel, or titanium. The material of the retention inserts and the configuration, such as shape and thickness, of any resiliently movable members of the inserts can be varied to vary the retention strength of the retention inserts. Accordingly, the retention strength of the retention inserts can be varied to accommodate different dental implant applications and preferences of the patient.

Figure 6:
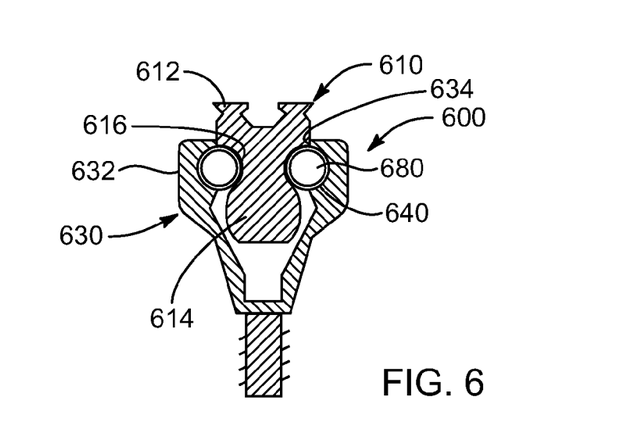
FIG. 6 is a cross-sectional side view of a dental prosthesis implant system having an o-ring retention device according to one embodiment.

Referring to FIG. 6, in some embodiments, the retention device is an o-ring 680 capable of being in frictional engagement with a male connector 610 and a female connector 630. The o-ring 680 is retained within an internal annular groove 640 formed in the socket portion 632 of female connector 630 proximate an inlet opening 634 of the female connector. The o-ring 680 is configured to engage an external annular groove 616 formed in the male connector 610 between a base 612 and a male engagement portion 614 of the male connector. When the male connector 610 is engaged with the female connector 630, the o-ring 680 engages the annular groove 616 to resist inwardly and outwardly directed movement of the male connector relative to the female connector. The o-ring 680 can have any of various hardness values each providing different resistances to deformation. When insertion or removal of the male connector 610 (e.g., denture) into or from the female connector 630 is desired, a respective inwardly or outwardly directed force sufficient to deform the o-ring 680 and respectively push or pull the male engagement portion 614 past the o-ring is applied to the male connector.

Figure 9:
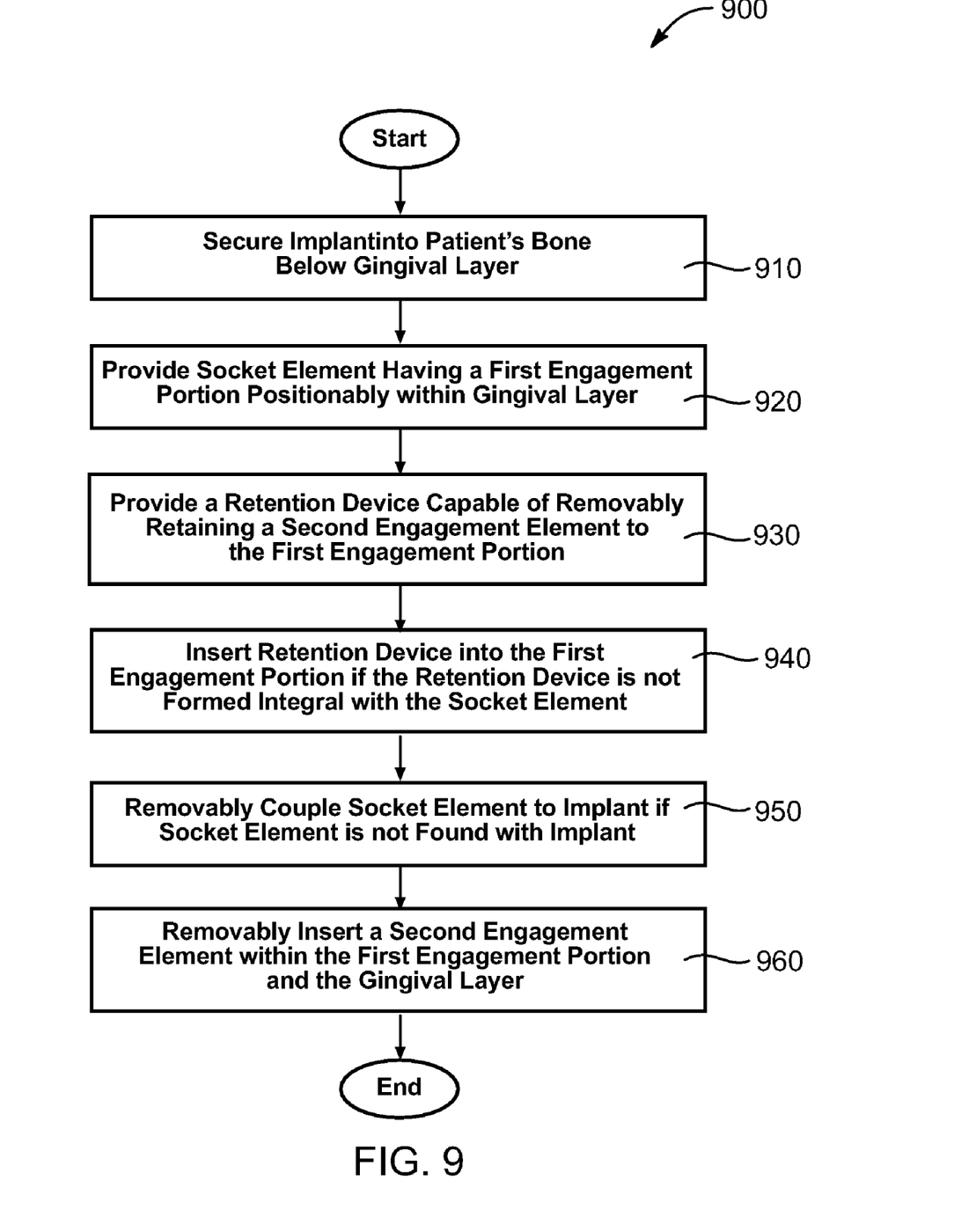
FIG. 9 is a schematic block diagram illustrating one embodiment of a method for implanting dental prosthesis.

Referring to FIG. 9, a method 900 for removably securing a dental prosthesis to a patient includes securing 910 a dental implant, such as implant 150, to a patient's jaw. In one embodiment, the implant is a self-tapping implant screwed through the patient's gingival layer (e.g., gingival layer 174 of FIG. 2) and into the patient's jaw bone under the gingival layer (e.g., bone 172 of FIG. 2). In other embodiments, a pilot hole, such as hole 172 (see FIG. 1), is first drilled into the gingival layer and underlying bone to facilitate embedding the implant into the bone. Referring to FIG. 2, the entire implant 150 or a substantial portion of the implant can penetrate the jaw bone 172 such that an upper portion of the implant is proximate an interface between the jaw bone and gingival layer 174. Although not particularly shown, the implant 150 can include tool engagement elements to facilitate embedding the implant into the bone using a fastening tool, such as a screwdriver-type tool or drill.

The method 900 further includes providing 920 a socket element having a first engagement portion positionable within the gingival layer. With reference to the embodiment of FIG. 2, the female connector 130, e.g., socket element, includes a first engagement element, e.g., socket portion 132. A portion of the socket portion 132 is positioned within the gingival layer 174, i.e., between an outer surface 176 of the gingival layer and the jaw bone 172.

According to the method 900, a retention device capable of removably retaining a second engagement element to the first engagement portion is provided 930. In certain instances, the retention device is one of retention device 180, 480, 580, 680, 780, 880. If the retention device is not formed integral with the socket element, then the method includes inserting 940 the retention device into the first engagement portion. For example, the retention device 180, not being formed integral with the female connector 130 (i.e., separate and disparate from the female connector), is inserted into the socket portion 132 within the internal cavity 142 (see FIGS. 1 and 2). Retention devices 580, 680, 780, are similarly inserted into respective socket portions 532, 632, 732 (see FIGS. 5, 6, and 7). However, retention device 480 is formed integral with the socket portion 432 of female connector 430 such that the retention device need not be inserted into the socket portion to couple the retention device 480 to the socket portion (see FIG. 4).

In the method 900, the socket element is removably coupled 950 to the implant if the socket element is not integrally formed with the implant. For example, referring to FIG. 1, the female connector 130 is not integrally formed with the implant 150. In other words, the female connector 130 and implant 150 are disparate elements. Accordingly, the female connector 130 is removably coupled to the implant 150 by inserting the fastener 136 into the threaded aperture 152 and tightening the female connector against the implant. The female connector 130 can be tightened by inserting a tightening tool, such as a hex wrench, into the internal recess 138 and rotating the tool. Generally, the implant 150 is first secured to the jaw bone 172 and then the female connector 130 is removably coupled to the implant. However, in some embodiments, the female connector 130 can be removably coupled to the implant 150 before embedding the implant into the jaw bone 172.

In certain embodiments, the female connector 130 can be removed from the implant 150 and replaced for any of various reasons. For example, the female connector 130 or associated retention device can be worn down over continued use or become damaged such that replacement or repair is desired. In situations where the strength of the retention device is reduced, the female connector 130 can be removed from the implant 150 and a female connector 130 with a retention device having a desirable strength can be coupled to the implant in its place.

In embodiments where the female connector 130 is integrally formed with the implant 150 as a one-piece construction, the implant and female connector are simultaneously embedded into the jaw bone 172 and gingival layer 174, respectively. A tightening tool can be inserted into the internal recess 138 and rotated to embed the female connector 130 in the gingival layer 174 and the implant 150 into the jaw bone 172 in a manner similar to that discussed above.

The female connector 130 can be configured such that a specific percentage of the female connector is within the gingival layer 174 and a specific percentage is above the gingival layer. The thickness of the gingival layer 174 can be different for different patients and at different locations along the jaw bone. Generally, however, the average gingival layer thickness for most patients is about two millimeters. Therefore, referring to FIG. 3, the total height $D_1$ of the female connector 130 is at least the thickness of the gingival layer 174, e.g., two millimeters. As shown, a portion of the female connector 130 can extend above or beyond the outer surface 176 of the gingival layer 172 a distance $D_2$. For example, in some embodiments, the total height $D_1$ of the female connector 130 is greater than the thickness of the gingival layer 174 such that the distance $D_2$ is equal to approximately the total height $D_1$ minus a predicted thickness of the gingival layer or the length of the female connector embedded within gingival layer, e.g., two millimeters. In other embodiments, the female connector 130 is flush with, e.g., does not extend past the outer surface 176 of, the gingival layer 174. In other words, in certain embodiments, the distance $D_2$ can be approximately zero. In specific exemplary embodiments, the total height $D_1$ can be between about two millimeters and about 8 millimeters and the distance $D_2$ can be between about zero millimeters and about 6 millimeters.

Figure 3:
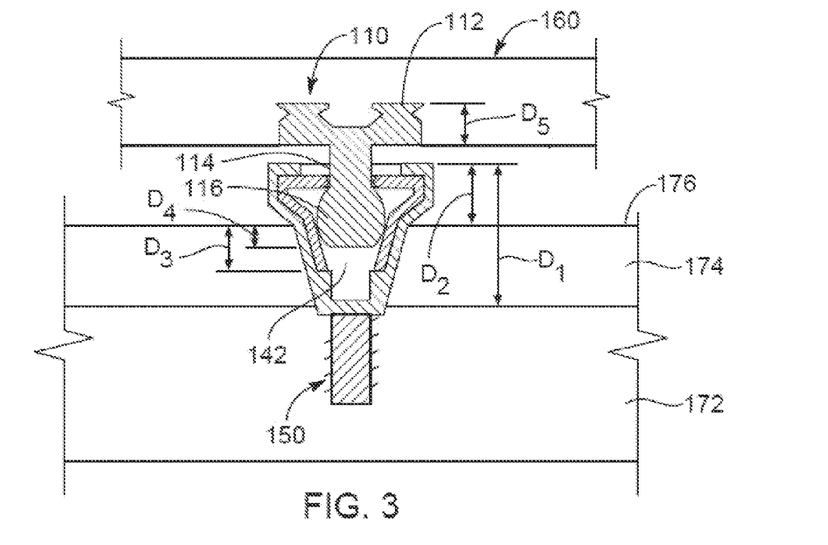
FIG. 3 is a cross-sectional side view of the system of claim 1 shown in an assembled state.

As shown in FIG. 3, when the implant 150 is embedded within the jaw bone 172 and the female connector 130 is secured to the implant, at least a portion of the internal cavity 142 is positioned within the gingival layer 174, or below the gingival line or outer surface 176. The portion of the internal cavity 142 positioned within the gingival layer 174 has a length or height $D_3$. In other words, the internal cavity 142 extends below the surface of the gingival layer 174 a distance $D_3$. The distance $D_3$ can be any of various distances. For example, in one exemplary embodiment, the distance $D_3$ can be greater than zero and less than about six millimeters for various gingival layer thicknesses, e.g., gingival layer thicknesses between about one millimeter and about 3 millimeters. In some embodiments, the implant 150 can be configured such that the internal cavity 142 extends below the gingival layer 174 and within the bone layer 172. Accordingly, in certain embodiments, the distance $D_3$ can be greater than 0% and less than about 400% of the thickness of the gingival layer 174. The portion of the internal cavity 142 within the gingival layer 174 can also be defined according to the percentage of the cavity's height that extends below the outer surface 176 of the gingival layer. For example, in one specific implementation, a substantial portion of the internal cavity's height, e.g., more than half of the height, extends below the outer surface 176 of the gingival layer. In other implementations, more or less than one half of the height extends below the outer surface 176 of the gingival layer.

The method 900 further includes removably inserting 960 a second engagement element coupled to a dental prosthesis within the first engagement portion and the gingival layer. For example, referring to FIGS. 2 and 3, the male engagement portion 114 of the male connector 110 is moved inwardly and inserted through the female connector inlet opening 134, through the retention device aperture 182, and into the internal cavity 142 of the socket portion 132. As the male engagement portion 114 is inserted through the retention device aperture 182, the ball-shaped engagement element 116 contacts and is pushed inwardly against the resiliently movable member or members 184 of the retention device 180. Once an inwardly force sufficient to overcome the biasing force of the resiliently movable members 184 is applied to the members 184 via the male engagement portion 114, the movable members 184 flex downwardly to widen the retention device aperture 182 and allow the element 116 to pass through the aperture 182. As the section of the element 116 with the largest dimension passes through the aperture 182, the movable members 184 return to the unflexed state. In certain instances, the movable members 184 snap back into the unflexed state to create an audible snap indicating the prosthesis 160 is secured to the female connector 130. In the unflexed state, the movable members 184 are biased to resist outward movement of the element 116.

To remove the dental prosthesis 160 from the patient's mouth, e.g., to remove the ball-shaped element 116 from engagement with the female connector 130, the prosthesis is pulled away from the jaw such that the element 116 is pushed outwardly against the resiliently movable member or members 184 of the retention device 180. Once an outwardly directed force sufficient to overcome the biasing force of the movable members 184 is applied to the members 184, the movable members 184 flex upwardly to widen the retention device aperture 182 and allow the element 116 to pass through the aperture 182. The retention devices 480, 580, 880 perform in a manner similar to retention device 180 during insertion, retention, and removal of the male connector.

The removable insertion 960 of a male engagement portion into and removal of the male engagement portion from the female connector 780 of FIG. 7 is performed in a manner similar to that discussed above. However, instead of flexing downwardly during insertion and outwardly during removal of the male engagement portion, the movable members 782 flex laterally away from each other during both insertion and removal procedures.

In the illustrated embodiments, the male engagement portion of a male connector is inserted into and retained within a socket portion of female connector such that at least a portion of the male engagement portion is within, e.g., under, the gingival layer. For example, as shown in FIG. 3, the male engagement portion 114 extends below the outer surface 176 of the gingival layer 174 a distance $D_4$. The length, size, and shape of the male engagement portion 114, as well as the internal cavity 142, can be varied to change the value of distance $D_4$. As with the internal cavity 142, in some implementations, the top of the anchor 150 can be within the bone layer 172 such that the male engagement portion 114 extends below the gingival layer 174 and into the bone layer 172. As an example only, in some representative embodiments, the distance $D_4$ is greater than zero and less than about six millimeters. The portion of the male engagement portion 114 within the gingival layer 174, as well as the bone layer 172, can also be defined according to the percentage of the male engagement portion, and more specifically the height of the ball-shaped engagement element, that extends below the outer surface 176 of the gingival layer, or even below the bone line. For example, in one specific implementation, a substantial portion of the male engagement portion 114, e.g., about half of the ball-shaped engagement element 116, extends below the outer surface 176 of the gingival layer 174. In other implementations, more or less than one half of the ball-shaped engagement element 116 extends below the outer surface 176 of the gingival layer 174.

Generally, because a portion of the internal cavity 142 and a portion of the male engagement portion 114 extend below the outer surface 176 of the gingival layer 174, the vertical space above the gingival layer 174 occupied by dental prosthesis connections is significantly reduced. Because less vertical space is required, the prosthesis can be placed much closer to the gingival layer 174 allowing for a more secure, comfortable, and aesthetically pleasing fit. Further, because the male connector 110 is fixed to the prosthesis 160, as opposed to the female connector 130, the prosthesis 160 design and manufacturing can be less complex and complicated. For example, in order to maintain a minimal distance between the gingival layer and the prosthesis, conventional female-type connectors fixed directly to the prosthesis mandate a significant portion of the connector to be formed into the prosthesis, which places limitations on the design of the prosthesis. Because the present system 100 does not directly fix the female connector to the prosthesis, the system requires only a small portion of the male connector 110 to be formed in the prosthesis. For example, the height $D_5$ of the base 112 formed in the prosthesis can be less than about 4 millimeters. In one specific implementation, the height $D_5$ is approximately one millimeter. In certain instances, a ratio of the height $D_5$ to the distance $D_2$ is less than about 0.50.

The schematic flow chart diagrams herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A connector for an implant retained prosthesis, comprising:
    a first portion securable to a prosthesis, the first portion comprising a first engagement element, wherein the first engagement element is immovably fixed relative to the prosthesis;
    a second portion securable to an implant embeddable within a bone, the bone being under a gingival layer and the second portion comprising a second engagement element defining an internal cavity, wherein the first engagement element is positionable within the internal cavity; and
    a retention device positioned within the internal cavity of the second engagement element, the retention device comprising an inlet and an internal cavity within which the first engagement element is removably retained, wherein the inlet is smaller than the first engagement element to removably retain the first engagement element within the internal cavity of the retention device and a portion of the internal cavity of the retention device adjacent the inlet is substantially larger than the first engagement element, the portion of the retention device defining the inlet being flexible to facilitate passage of the first engagement element through the inlet;
    wherein when the second portion is secured to the implant and the first engagement element is positioned within the internal cavity, at least a portion of the internal cavity and first engagement element is within the gingival layer.

2. The connector of claim 1, wherein the second engagement element comprises a thin-walled overhang defining an inlet of the internal cavity of the second engagement element, and wherein the thin-walled overhang retains the retention device within the internal cavity of the second engagement element.

3. The connector of claim 1, wherein the portion of the retention device defining the inlet flexes inwardly away from the prosthesis to facilitate passage of the first engagement element through the inlet in a first direction, and the portion of the retention device defining the inlet flexes outwardly toward the prosthesis to facilitate passage of the first engagement element through the inlet in a second direction opposite the first direction.

4. The connector of claim 1, wherein the retention device comprises an insert nestably engaged with the second engagement element.

5. The connector of claim 1, wherein the retention device comprises at least one resiliently movable element.

6. The connector of claim 1, wherein the portion of the retention device defining the inlet flexes radially outwardly to facilitate passage of the first engagement element through the inlet.

7. The connector of claim 1, wherein the retention device comprises a plurality of resiliently movable elements.

8. The connector of claim 1, wherein the second portion forms a monolithic one-piece construction with the implant.

9. The connector of claim 1, wherein the first engagement element comprises a ball and the second engagement element comprises a socket.

10. The connector of claim 1, wherein when the second portion is secured to the implant and the first engagement element is positioned within the internal cavity, the second portion extends a distance less than about six millimeters out of the gingival layer.

11. The connector of claim 1, wherein the height of the second portion is less than the height of the first portion.

12. The connector of claim 1, wherein the first portion is coupleable to the second portion via a snap-fit connection.

13. A system for an implant retained prosthesis, comprising:
    a connection comprising:
        a prosthesis connection comprising a ball and a bonding surface configured to bond to a dental prosthesis, the ball and bonding surface being immovably fixed relative to the prosthesis;
        an abutment comprising a socket defining an internal cavity configured to receive the ball; and
        a retention device configured to removably retain the ball within the abutment, wherein the retention device is positioned within the internal cavity of the abutment, the retention device comprising an inlet and an internal cavity within which the ball is removably retained, and wherein the inlet is smaller than the ball to removably retain the ball within the internal cavity of the retention device and a portion of the internal cavity of the retention device adjacent the inlet is substantially larger than the first engagement element, the portion of the retention device defining the inlet being flexible to facilitate passage of the first engagement element through the inlet; and
    an implant connectable to the abutment and embeddable within a bone, the bone being covered by a gum layer having an outer surface;
    wherein when the implant is embedded within the bone and the implant is connected to the abutment, at least a portion of the internal cavity is positioned between the bone and the outer surface of the gum layer.

14. The system of claim 13, wherein the retention device comprises a compliant material.

15. The system of claim 14, wherein the retention device comprises a polymeric material.

16. The system of claim 13, wherein the retention device is removably retained within the abutment.

17. The system of claim 13, wherein the retention device comprises a snap insert configured to generate an audible signal in response to the ball being removably retained within the retention device.

18. The system of claim 13, wherein when the implant is embedded within the bone, the implant is connected to the abutment, and the ball is removably retained within the retention device, at least a portion of the ball is positioned between the bone and the outer surface of the gum layer.

19. The system of claim 18, wherein when the implant is embedded within the bone, the implant is connected to the abutment, and the ball is removably retained within the retention device, at least one-half of the internal cavity and at least one-half of the ball are positioned between the bone and the outer surface of the gum layer.

20. The system of claim 13, wherein the abutment extends outward beyond the outer surface of the gum layer a first distance and the prosthesis connection extends into the prosthesis a second distance, and wherein the ratio of the second distance to the first distance is less than about 0.50.

21. A method for securing prosthesis to a patient, the method comprising:
fixedly securing an implant to a bone of the patient, the bone being covered by a gingival layer defining an outer surface;
coupling a socket element having a female engagement portion to the implant, wherein at least a portion of the female engagement portion is between the bone and the outer surface of the gingival layer;
coupling a retention device to the female engagement portion by positioning the retention device within an internal cavity of the female engagement portion, the retention device comprising an inlet and an internal cavity; and
inserting a male engagement portion of a connector element through the inlet and into the internal cavity of the retention device such that at least a portion of the male engagement portion is between the bone and the outer surface of the gingival layer, the inlet being smaller than the male engagement portion, wherein a portion of the internal cavity of the retention device adjacent the inlet is substantially larger than the male engagement portion, the portion of the retention device defining the inlet being flexible to facilitate passage of the male engagement portion through the inlet, wherein the connector element is immovably secured to a prosthesis, and wherein inserting the male engagement portion into the female engagement portion comprises engaging the male engagement portion with the retention device such that the male engagement portion is removably retained within the female engagement portion.

22. The method of claim 21, wherein inserting the male engagement portion into the female engagement portion comprises resiliently flexing the portion of the retention device defining the inlet inwardly away from the prosthesis.

23. The method of claim 22, wherein the socket element is a first socket element and the retention device is a first retention device, the method further comprising removing the first socket element from the implant and coupling a second socket element to the implant, wherein the second socket element has a second retention device different than the first retention device coupled thereto.

24. The method of claim 21, wherein coupling a socket element to the implant comprises forming the socket element integral with the implant.

\* \* \* \* \*